(12) United States Patent
Verenchikov

(10) Patent No.: US 9,417,211 B2
(45) Date of Patent: *Aug. 16, 2016

(54) ION MOBILITY SPECTROMETER WITH ION GATE HAVING A FIRST MESH AND A SECOND MESH

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,038

(22) Filed: Dec. 30, 2014

(65) Prior Publication Data

US 2015/0115151 A1    Apr. 30, 2015

Related U.S. Application Data

(63) Continuation of application No. 14/356,015, filed as application No. PCT/US2012/063345 on Nov. 2, 2012, now Pat. No. 8,921,772.

(60) Provisional application No. 61/554,770, filed on Nov. 2, 2011.

(51) Int. Cl.
*H01J 49/00* (2006.01)
*G01N 27/62* (2006.01)
(Continued)

(52) U.S. Cl.
CPC .............. *G01N 27/622* (2013.01); *G01N 30/72* (2013.01); *G01N 30/7206* (2013.01); *H01J 49/0031* (2013.01); *H01J 49/406* (2013.01)

(58) Field of Classification Search
CPC ........ H01J 49/00; H01J 49/02; G01N 27/622; G01N 27/624
USPC .......................... 250/281, 282, 283, 286, 290
See application file for complete search history.

(56) References Cited

U.S. PATENT DOCUMENTS

| 2007/0176090 | A1  | 8/2007  | Verentchikov |              |
|--------------|-----|---------|--------------|--------------|
| 2007/0278397 | A1* | 12/2007 | Bateman      | G01N 27/622  |
|              |     |         |              | 250/286      |
| 2009/0294662 | A1* | 12/2009 | Belov        | H01J 49/4235 |
|              |     |         |              | 250/291      |
| 2011/0095175 | A1* | 4/2011  | Bateman      | G01N 27/624  |
|              |     |         |              | 250/282      |

FOREIGN PATENT DOCUMENTS

| JP | 2007-534126   | 11/2007 |
| JP | 2009-2815     | 1/2009  |
| WO | WO-2005104182 | 11/2005 |

OTHER PUBLICATIONS

Japan Office Action dated Mar. 20, 2015, relating to Japanese Patent Application. No. 2014-540141.

(Continued)

*Primary Examiner* — Nicole Ippolito
*Assistant Examiner* — Jason McCormack
(74) *Attorney, Agent, or Firm* — Honigman Miller Schwartz and Cohn LLP

(57) ABSTRACT

A method and apparatus are disclosed for improving ion mobility spectrometry by using a fast and spatially wide ion gate based on local RF field barrier opposed to a switching DC field. The improvement accelerates the ion mobility analysis and improves charge throughput and dynamic range of the IMS. The invention is particularly suited for rapid dual gas chromatography. In one important embodiment, the accelerated IMS is coupled to a multi-reflecting time-of-flight mass spectrometer with a fast encoded orthogonal acceleration. There are described methods of comprehensive and orthogonal separation in multiple analytical dimensions.

21 Claims, 6 Drawing Sheets

(51) Int. Cl.
*G01N 30/72* (2006.01)
*H01J 49/40* (2006.01)

(56) References Cited

OTHER PUBLICATIONS

"Rapid determination of complex mixtures by dual-column gas chromatography with a novel stationary phase combination and spectrometric detection", G.R. Lambertus, et al, Journal of Chromatography, Elsevier Science Publishers B.V., NL, Dec. 1, 2006.

"Real-time trace detection of security-relevant compounds in complex sample matrices by thermal desorption—single photon ionization—ion trap mass spectrometry (TD-SPI-ITMS) Spectrometry (TD-SPI-ITMS)", Elisabeth Schramm, et al, Analytical and Bioanalytical Chemistry, Springer, Berlin, DE, Jul. 9, 2009.

International Search Report dated Apr. 25, 2013, relating International Application No. PCT/US2012/063345.

* cited by examiner

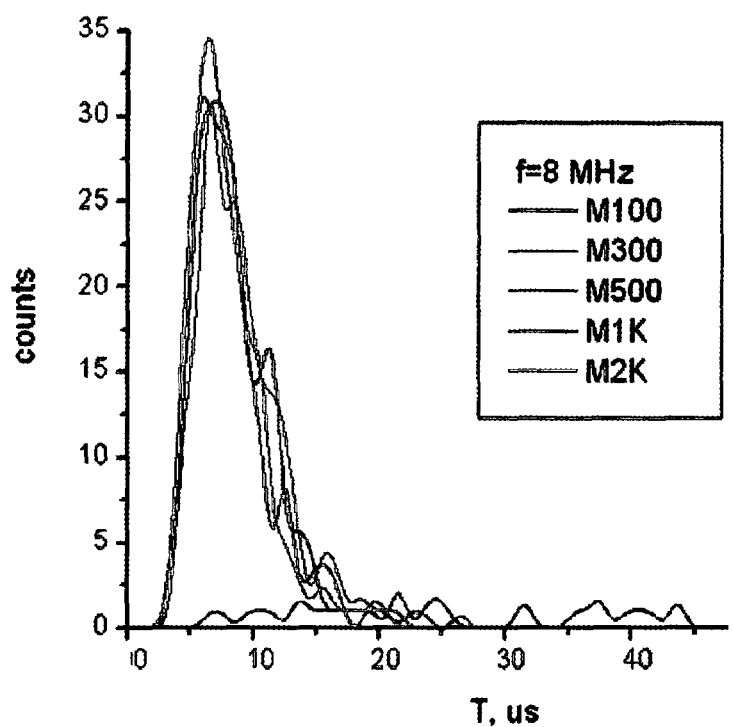
*Fig.4-A*
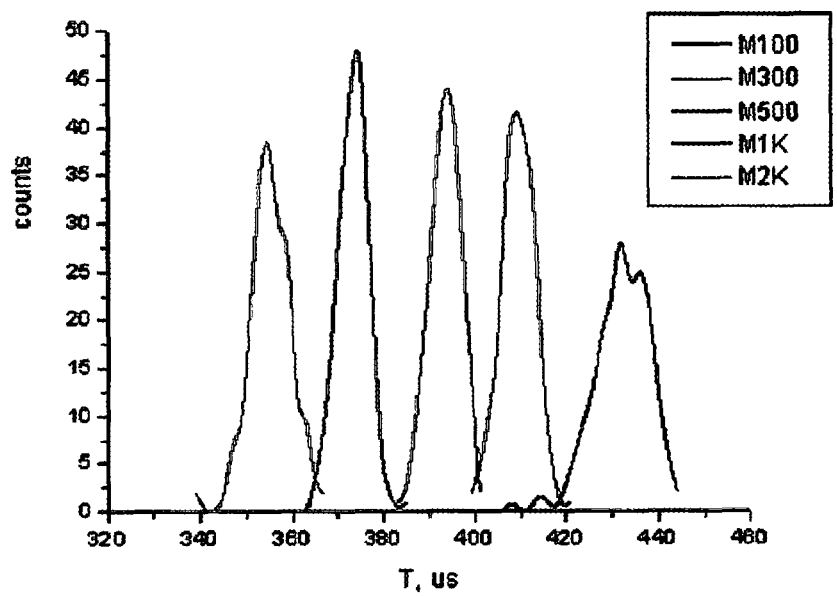
*Fig.4-B*

ION MOBILITY SPECTROMETER WITH ION GATE HAVING A FIRST MESH AND A SECOND MESH

I. TECHNICAL FIELD

This disclosure generally relates to the area of ion mobility spectrometry and to improvements ion mobility spectrometry for coupling with multidimensional gas chromatography and mass spectrometry.

II. BACKGROUND

Ion mobility spectrometers (IMS) are widely used for analyzing ionized compounds by their mobility, which is the function of ion charge, mass and shape. Typical IMS comprises an ion source for soft ionization of analyte compounds, an ion gate (typically Tyndal gate) to form short ion packets, a gas filled drift tube for ion separation in electrostatic fields, and a collector to measure time dependent signal. As a stand-alone analytical technique, IMS has low resolution (50-100). IMS was primarily considered as a low cost hand-held detector of toxic volatile compounds, with low detection limits that may be enhanced by specific ion molecular reactions with doping vapors. More recently IMS has been coupled with gas chromatography (GC), liquid chromatography (LC) and mass spectrometry (MS), where IMS brings an additional dimension of analytical separation. However, the straight forward coupling can cause strong signal losses in IMS due to ~1% duty cycle of Tyndal ion gate and mismatch in gas pressures and ion cloud size between IMS and MS. If using scanning MS, like quadrupoles, there occurs a mismatch in time scales.

U.S. Pat. No. 5,200,614, incorporated herein by reference, discloses improvement of IMS sensitivity by trapping ions between gate pulses. U.S. Pat. No. 3,902,064, incorporated herein by reference, discloses a combination of IMS spectrometer with the downstream mass spectrometer for complimenting mobility measurements by ion mass measurements. Young, et. al. in paper J. Chem. Phys., v. 53, No 11, pp. 4295-4302, incorporated herein by reference, discloses a combination of IMS spectrometer with the downstream orthogonally accelerating time-of-flight detector which is capable of fast recording of panoramic (all mass) spectra for higher speed and duty cycle of mass measurements. U.S. Pat. No. 5,905,258, incorporated herein by reference, discloses a combination of both features—an ion trap in-front of the IMS and orthogonal TOF past IMS, thus capitalizing on both advantages—higher duty cycle of IMS and MS.

U.S. Pat. No. 6,107,628, incorporated herein by reference, discloses an ion funnel device for converging ion flows at intermediate gas pressures. U.S. Pat. No. 6,818,890, incorporated herein by reference, discloses an ion funnel for ion confinement past IMS. Paper Anal. Chem., 2008, v. 80, pp. 612-623, incorporated herein by reference, describes usage of the ion funnel device for both—for ion trapping prior to IMS and for ion confinement past the IMS. Details on the so-called hourglass ion funnel trap are also presented in Anal. Chem., 2007, v. 79, pp. 7845-7852, incorporated herein by reference. The described method presents the ultimately sensitive IMS-MS of prior art, which still suffers several limitations. The number of trapped ions is limited by the space charge capacity of the ion trap and of IMS drift tube to 1E+7 charges per pulse. Both the hourglass gate and downstream ion funnel spread ion packets to about 200-400 us, which slows down the IMS speed, leads to long drift separation times of at or around 20-40 ms, requires constructing long (about 1 m long) IMS drift tubes, and limits the IMS charge throughput and the dynamic range.

WO2008112351, incorporated herein by reference, discloses a method of improving IMS dynamic range and space charge capacity by multiplexed coding of the ion trap which operates at much higher net frequency compared to conventional regime of single trap firing per IMS separation. However, the approach requires ion packets overlapping and is likely to cause confusions at data interpretation.

Summarizing the above, IMS and IMS-TOF of prior art are limited in their charge throughput, dynamic range and speed, which limits their combination with fast separation methods. Therefore, there is a need for improving IMS and IMS-TOF parameters.

III. SUMMARY

The charge throughput and the speed of IMS can be increased by forming much shorter, spatially uniform and wider ion packets. A gate is disclosed comprising a dual mesh with an RF signal applied between meshes, thus forming an RF barrier for ions at gas pressures from 1 to 100 mBar. In an implementation, ions can be either pulsed ejected to form 10-20 us packets, or released in a mass-dependent fashion by a ramped DC field. Formation of short ion packets potentially allows shortening the IMS spectrometer in size and obtention of an order of magnitude faster speed (1-2 ms cycles), higher throughput, and dynamic range—all helpful for implementation rapid upfront separating devices (e.g., dual GC separation) for rapid surface analysis and/or for tracking rapid in-source reactions.

In an implementation, to support the speed, preferably a shorter (10-20 cm) IMS drift tube may be used in combination with a higher gas pressure (10-100 Torr). A small cell (0.1-1 mm) grid is expected to provide an RF barrier at such elevated pressures.

In an implementation, to support the speed of operation, ions (entrained into a gas jet) are introduced from a side of the gate, such that ions would be passing above the gate. The arrangement is expected to eliminate any carry-over between ejection cycles and allows removing light ions, which are likely to carry most of the current.

In one group of embodiments, the IMS is preceded either by a fast separating chromatography, like dual GC, or by a second slower separating IMS, optionally with a fragmentation cell in-between, or by an ion source which generates rapid changes in ion composition, like sources for rapid surface scanning, or ion sources generating chemical or ion molecular reactions at time scale down to milliseconds.

In another group of embodiments, the IMS is followed by a time-of-flight mass spectrometer, preferably a multi-pass TOF MS, equipped with a coded fast pulsing. Such mass spectrometers are capable of tracking changes down to 5-10 us time scale. To support the speed of IMS separation and to reduce ion packet time spread, the IMS exit section is equipped with either an ion funnel having central section, or converging multipole built as a stack of printed circuit boards, preferably followed by a conductive ion guide with axial field gradient. In one group of embodiments, a mass dependent gate release allows simultaneous injection into MR-TOF of ions with correlated m/z and mobility. In one group of particular embodiments, a fragmentation cell is used to fragment IMS separated ions.

In an implementation, there is provided a fast ion mobility spectrometer (IMS) matching high speed of GC×GC analysis at time scale (30-50 ms). Said fast IMS sequentially comprises: an ion source, said source being filled with gas at gas pressure from 1 mBar to 1 Bar; an ion gate formed of a front cap electrode, followed by a front mesh and then by a back mesh; said meshes are parallel and spaced at a distance comparable to mesh cell size; a radiofrequency (RF) generator connected to said front mesh; a switching DC signal connected to said cap electrode and said back mesh; an ion drift space filled with gas at pressure from 1 to 30 mBar; and an ion detector.

The dual RF mesh gate is expected to save IMS duty cycle and generate short (~10 us) ion packets, this way improving IMS speed, charge throughput and dynamic range. Preferably, said ion source may be oriented substantially parallel to said meshes. Preferably, the apparatus may further comprise at least one RF ion guide between said ion source and said ion gate, and wherein said RF ion guide comprise one of the group: (i) an ion funnel; (ii) a multipole ion guide with axial field. Preferably, the apparatus may further comprise either an upfront gas chromatograph or an upfront dual stage gas chromatograph; and wherein the region of said ion gate and of said drift space is pumped by a mechanical pump. Preferably, said ion source may comprise one of the group: (i) a photoionization source; (ii) a photo-chemical ionization source with a dopant; (iii) a chemical ionization source with proton transfer reactions; (iv) a chemical ionization source with electron attachment ionization; (v) a glow discharge source with analyte ionization by conditioned products of glow discharge. Preferably, said source may have means for switching between ionization modes or for switching between ion polarities. Preferably, said source may have fragmentation means and means for switching said fragmentation at time scale of chromatographic separation.

In another implementation, there is provided a tandem of fast IMS and MR-TOF for matching time scale of GC×GC analysis. Such apparatus comprises the above described IMS with the fast dual mesh gate; an ion mobility drift spectrometer; a tapered IMS section for converging an ion flow; an orthogonal accelerator with fast coded pulsing at mean frequency exceeding 100 kHz; a multi-reflecting time-of-flight mass spectrometer; and a data system providing coded start signals with the string duration comparable to IMS separation time and also providing IMS-MS spectral decoding with the account of the coded pulse intervals.

The pulse coded TOF is expected to match the speed of the fast IMS without ion losses. Preferably, said tapered IMS section may comprise either an ion funnel with a central expanding and contracting section, or a PCB made multipole set with an axial DC gradient formed of multipole sections with a DC offset linearly changing along the multipole set.

In an implementation, there is provided a method of rapid ion mobility spectrometric analysis, sequentially comprising the following steps: generating ions within an ion source operating at gas pressure from 1 mBar to 1 Bar; forming a local RF field between closely spaced parallel meshes while attracting ions toward the RF field region by a DC field which is sufficiently small to prevent ion penetration through the barrier of said RF field and this way causing ion localization in local RF traps around mesh cells; propelling ions through said RF field by a pulsed switch of a DC field in the region of said RF field, thus forming short ion packets; separating ions by their mobility within an electrostatic field at gas pressure from 1 to 30 mBar; and detecting a time dependent signal on a detector.

Preferably, ions may be introduced into the RF field region substantially parallel to said mesh plane. Preferably, the method may further comprise a step of ion transfer between said ionization and said gating steps; said transfer step is assisted by radiofrequency confinement of ions in order to adopt a difference between gas pressures and to avoid significant gas motion within the mobility separation stage. Preferably, the method may further comprise a step of analyte separation either by a method of gas chromatographic separation or by a method of dual stage gas chromatographic separation. Preferably, said ionization step may comprise one step of the group: (i) a photoionization; (ii) a photo-chemical ionization with a dopant; (iii) a chemical ionization with proton transfer reactions; (iv) a chemical ionization with electron attachment ionization; and (v) analyte ionization by conditioned products of a glow discharge. Preferably, the method may further comprise steps of switching between ionization methods or of switching between ion polarities. Preferably, the method may further comprise a step of ion fragmentation being switched on and off at time scales of said chromatographic separation.

In an implementation, there is provided a method of IMS-MR-TOF analysis at GC×GC time scale. Said method comprises steps as described above in connection with the fast IMS method and further comprises the steps of: spatial focusing of ion flow past said step of ion mobility separation; orthogonal ion acceleration with repeatable strings of fast coded pulses at mean frequency exceeding 100 kHz; time-of-flight analysis of ion m/z within a multi-reflecting electrostatic fields; and of decoding information on ion mobility time, ion mass and ion intensity based with the account of the coded pulse intervals.

Preferably, the method may further comprise a step of ion fragmentation between steps of ion mobility separation and step of time-of-flight analysis. Preferably, the method may further comprise a step of ion sequence inversion at slow ramping of DC field propelling ions through said RF barrier at said gating step.

BRIEF DESCRIPTION OF THE DRAWINGS

Various embodiments of the present invention together with arrangement given illustrative purposes only will now be described, by way of example only, and with reference to the accompanying drawings in which:

FIG. 4A depicts exemplary profiles for effective RF potential in the ion trapping gate;

FIG. 4B depicts DC potential profiles at a stage of ion passage through the gate;

IV. DETAILED DESCRIPTION

Figure 1:
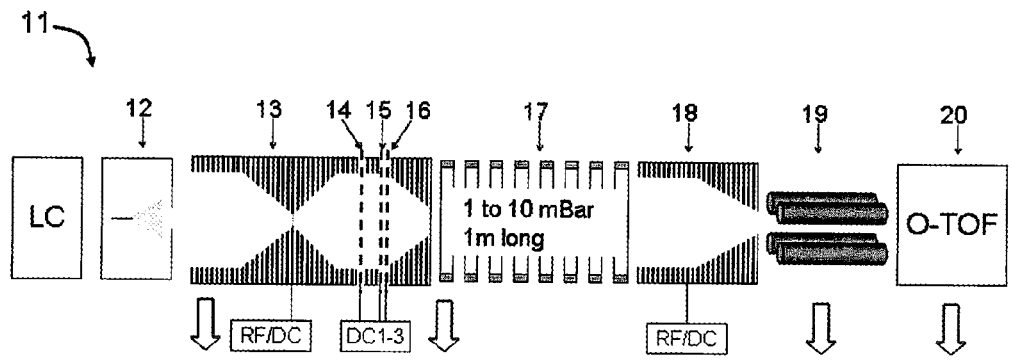
FIG. 1 depicts an IMS with an hourglass ion trap and ion funnel at the IMS exit.

Referring to FIG. 1, a prior art (Anal. Chem., 2008, v. 80, pp. 612-623, incorporated herein by reference) tandem 11 ion mobility spectrometer (IMS)—time-of-flight mass spectrometer (TOF MS) is shown comprising: an ion source 12, an hour-glass shaped ion funnel 13 connected to an RF signal having a superimposed axial DC gradient, incorporated between funnel plates three meshes 14, 15 and 16 connected to switched DC signals for ion gating; an ion drift tube 17 filled with gas at pressure from 1 to 10 mBar, a second ion funnel 18 for converging the ion flow, a differentially pumped quadrupole ion guide 19 at gas pressure of 10-100 mTorr, and a differentially pumped time-of-flight mass spectrometer with an orthogonal acceleration 20. Pumping is shown by white arrows. Some of RF and DC supplies are shown by boxes. Electrospray (ESI) ion source is shown by schematic view of ESI droplet plume, and the gas jet past the source—by a light colored cone.

In operation, liquid chromatograph (LC) separates analyte molecules in about 1 hr time, while typical width of LC peaks may be 5 to 20 sec wide. ESI ion source 12 ionizes analyte molecules while generating either M+ or MH+ ions. Ions are delivered by gas jet via a nozzle into the first ion funnel 13 region and get confined by the ion funnel 13. The gate accumulate ions in-front of the mesh 15 due to the weak (few Volts) DC bias between meshes 15 and 16. An extracting pulse is periodically applied to meshes 14 and 16 to drive ions through the mesh gate. Ions are then separated by mobility in the drift tube 17, get spatially confined by the second ion funnel 17, get transferred via the guide 19 and then analyzed by the TOF 20.

Typical 1 m length of the drift tube and typical 20 ms IMS drift times are required to reach resolution of 30 to 50, since typical width of ion packets is 200-400 us. The ion packet width is limited by several factors, including: (a) ion packet spreading by space charge in the IMS drift tube; (b) ion packet spreading within the second ion funnel 18 and within the quadrupole ion guide 19, and (c) by a slow (100 us) pulsing period of the TOF. Such separation speed is adequate if using an upfront liquid chromatography (LC), however, it is not sufficient for use with faster separation methods like GC×GC. The DC gate of IMS 11 is capable of storing and ejecting up to 1E+7 ions per pulse. However, because of ring shape of ion clouds, such ion loads are expected to affect resolution of IMS separation due to space charge effects in the drift tube.

Fast Gate and Fast IMS

Figure 2:
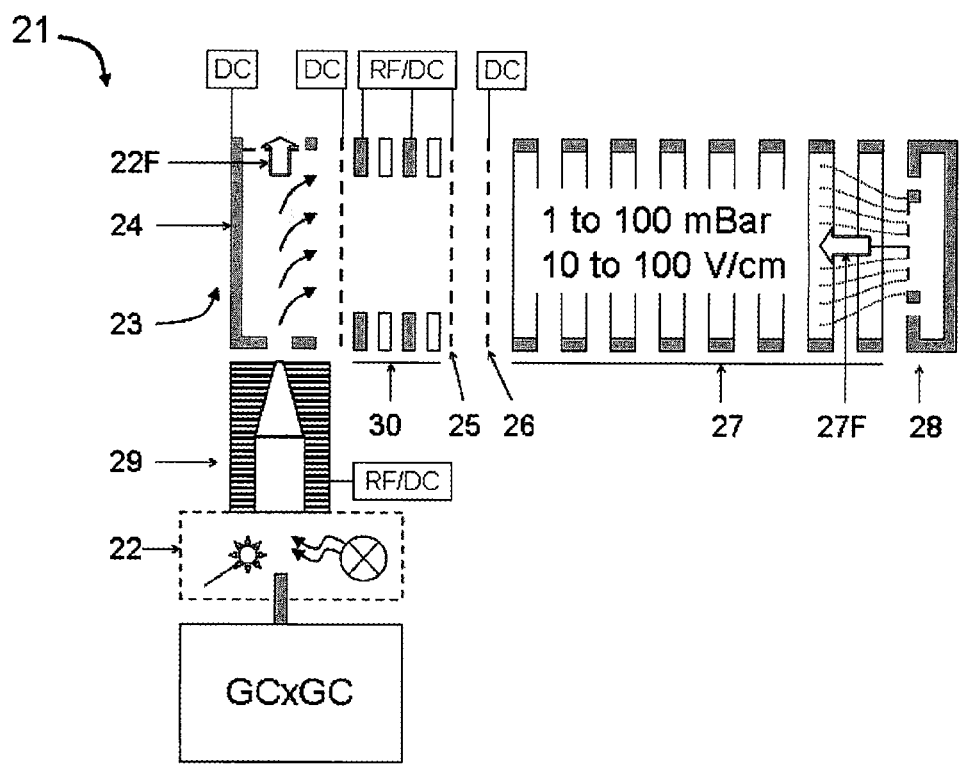
FIG. 2 depicts an embodiment of a dual mesh gate with an RF field therebetween.

Referring to FIG. 2, an embodiment 21 of an IMS is shown comprising: an ion source 22; an ion gate 23 formed of a front DC cap 24 electrode, a front mesh 25 with an RF potential and a back mesh 26 with a DC bias; a drift tube 27 formed of DC biased guarding rings to generate a generally uniform electrostatic field (substantially at or between 10 to 100 V/cm) and filled with gas at pressure from substantially at or between 1 to 100 mBar; and an ion detector 28—a collector electrode connected to an amplifier and signal recorder. In an implementation, to reduce time constant RC and capacity C of the collector, the electrode is made of fine mesh. In an implementation, the mesh may be backed by an electron having a retarding DC potential which facilitates substantially full ion collection. In an implementation, the collector mesh facilitates the formation of a generally uniform counter-flow gas flow 27F along the drift region 27 (~1 m/s). As depicted, power supplies are shown as schematic boxes.

In an implementation, the IMS is preceded by a dual stage gas chromatograph (GC×GC) for rapid separation of analyte mixtures. In an implementation, typical width of chromatographic peaks is substantially at or between 30-50 ms. After separation in GC×GC, the source 22 ionizes semi-volatile analyte molecules substantially at or between 100-1000 mBar gas pressure. A gas flow 22F delivers ions into the gate 23 region operating substantially at or between 10-100 mBar region. Preferably ions are focused by an ion funnel 30. Preferably, the gas flow 22F is oriented parallel and above the mesh 25, such that to keep meshes in a flow-quite zone. In the illustrated embodiment, a DC bias applied to cap electrode 24 pushes ions from the gas jet 22F towards the meshes as shown by arrows. Preferably, an RF channel 30 (with an entrance DC mesh) is inserted between the DC cap 24 and mesh 25 to avoid gas steering by the jet 22F.

In an implementation, the mesh 26 shields the mesh 25 from the strong (e.g., 10-100 V/cm) electrostatic field of the drift tube 27. The RF signal applied to mesh 25 forms a strong RF field between closely spaced meshes 25 and 26 thus retards ions in the close vicinity of meshes. A balance of the long acting and attracting DC field with short acting and repelling RF barrier forms the ion trapping region in the close vicinity of the front mesh 25. For a pulsed ion ejection, a pulsed DC bias is applied to cap 24 (or front mesh of the RF channel 25), and/or mesh 26. For a mass-dependent release, the DC bias is ramped smooth.

Figure 3:
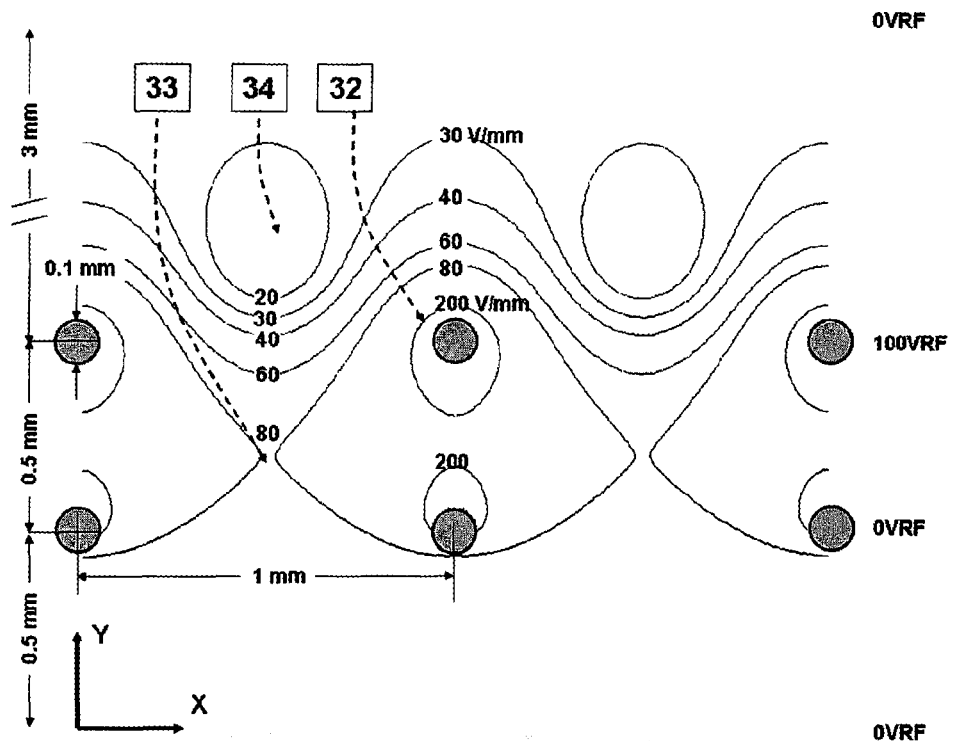
FIG. 3 depicts lines of equal field strength within the ion trapping gate.

With reference now to FIG. 3, the lines of equal field strength within the ion trapping gate 23 are shown for one chosen exemplar gate with 1 mm distance between meshes, 0.1 mm wire thickness and 0.5 mm distance between wires in each mesh, and at 100V amplitude of the RF signal Lines of equal field strength E are annotated by numbers. The effective potential of the RF field is known to be proportional to $E^2q/mD^2$, where q and m—ion charge and mass, D—is the RF frequency. Thus, higher field strength corresponds to a higher potential and ions get retarded from regions of higher field strength. Also note that the RF potential is mass dependent. As depicted, there is formed a retarding RF wall 32 around wires, there is also formed a saddle barrier 33 in the center between wires which prevents ion penetrating through the RF barrier at sufficiently small DC field. Further, there is also formed an RF trapping region 34, in which the RF signal is eliminated (quadrupole origin of the RF field) and DC fields of the cap 24 and of the back mesh 26 can be balanced. The graphs show vertical $E^2(Y)$ profiles at various X distance from wire center. The above described regions 32-34 of the trapping gate are indicated on the graph.

FIG. 4A shows time profiles for ion current past the gate at a stepped ejection by 50V pulse applied to the mesh 26, at gas pressure of 10 mBar, and at 100 V/cm DC field of the drift tube 27. Note that ion packets can be as short as 10 us, which is explained by precise localization of ions in trapping region 34 prior to the ejection step. FIG. 4B shows time profiles of various m/z ions with cross section proportional to $(m/z)^{2/3}$, and at a ramped DC ejection with the DC potential on the mesh 26 varied as 0.2 V/us. Since the effective potential of the RF barrier is mass dependent, the small m/z ions would pass first, which generates a mass inversion. In one particular method, the inversion is arranged such that ions with a particular ratio of mass and mobility arrive to the detector simultaneously. Such method is particularly suited for IMS-MS combinations described below.

Multiple other arrangements of meshes are contemplated. In an implementation, wire sets may be either aligned or shifted half step in the transverse direction. To avoid parallel alignment of two wire sets, the second mesh may be a square cell mesh with a much finer cell. The first mesh may be a mesh with crude cells having square, rectangular, or hexagon shapes. The RF signal may be applied to the second mesh as well, which would have negligible effect onto the ion motion in the drift region. Ion trapping stage may be assisted by a small retarding DC bias between meshes. The ejecting DC field may be applied to either a cap, or any of meshes.

Numerical Example and IMS Parameters

With continued reference to FIG. 2, in one numerical example, the distance between meshes 25 and 26 is 0.5 mm and mesh 25 is formed by parallel 50 um wires spaced at 1 mm. The open area of the gate is 50 mm in diameter. The RF signal on mesh 25 has 8 MHz frequency and 100V amplitude. The cap 23 is at 10 m distance from the mesh 25 and has potential of 2-10V. The field strength in the drift region is 100 V/cm at L=20 cm drift length and 2 kV across the drift. Gas pressure of about 10 mBar is sustained by mechanical pump in both—drift and gate regions, wherein 2000V across 20 cm is not expected to cause electrical breakdown. At such gas pressures the average ion mobility of relatively small ions (analyte is separated in GC) is in the 100 $cm^2N*s$ range. The average ion drift velocity is 100 m/s, i.e. notably under thermal gas velocity. The average drift time is 2 ms. The detector is 30-50 mm disk (assuming ion focusing by increasing electrostatic field at the IMS exit) connected to an electrometer with the 1 MOhm impedance. An expected detector capacity is 10 pF and the time constant of the electrometer is 10 us.

An estimation will now be provided to estimate whether such IMS can yield a target resolution R=T/dT from 50 to 100. First, the initial packet width $dT_0$<10 us does not limit R up to 200 at T=2 ms. Second, according to Einstein equation, the diffusion limit R<sqrt(U/kT) allows R~250 at U=2 kV. To sustain the same resolution limit by the ion packet space charge, the space charge field has to be less than 1 V/cm, i.e. at least 200 times smaller than the external field (accounting expansion of both—front and back ends). Such field is reached at maximal charge density of $4E+5 charges/cm^2$, and the entire 5 cm size packet is limited to 1E+7 charges per ion packet of individual mobility. This corresponds to 1 nA current throughput at 1-2 ms period and matches ion currents generated in majority of soft ionizing sources, like photo-chemical ionization, corona, and glow discharge ion sources. Still, it is preferable removing light by-generated ions by an additional mass filter. Such filter may be arranged with the same dual RF mesh located upstream of the IMS gate. Retarded ions may be blown off by a gas jet coming from the source. The same filter may be employed for controlling the amount of injected current either by balancing DC and RF fields with gas flow or by a pulsed and ion admission at 10-100 kHz rate.

The dynamic range of IMS is limited by maximal signal on high end (defined by space charge limit of 1E+7 ions per pulse per component) and by the detector amplifier noise on low end. The Jonson noise of an amplifier is about 30 uV at 100 kHz bandwidth (matching IMS peak width and filtering out RF signal of the gate). The maximal signal of 1E+7 charges (1.6 pC) at 10 us time corresponds to 1.6 uA current and 1.6V signal at 1 MOhm impedance. Thus, the dynamic range per single IMS shot is limited to approximately 10,000 assuming S/N=3 as detection threshold.

According to the above estimations, the IMS 21 is expected to operate at 1-2 ms period and to provide sufficient time resolution in GC×GC-IMS experiments, wherein the peak width past GC×GC 29 is expected in the range from 30 to 50 ms.

Figure 5:
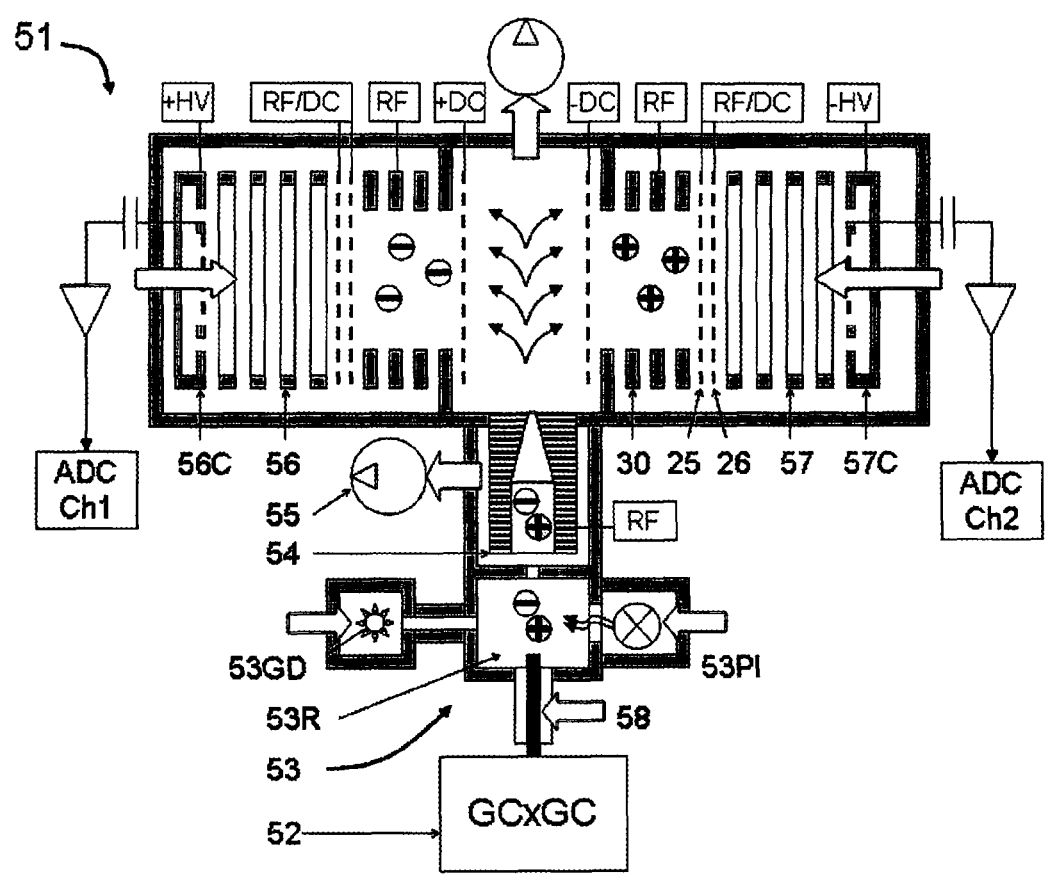
FIG. 5 depicts an embodiment of IMS with dual mode ion source and dual drift cell.

Referring to FIG. 5, an embodiment 51 of an ion mobility spectrometer is shown comprising a GC or GC×GC separator 52, a combined ion source 53 with multiple ionization modes and switching polarity of ionization. As depicted, such switching is preferably made between IMS scans. In an implementation, source 53 operates at gas pressures from substantially at or between 100 mBar to 1 Bar. As will be appreciated after considering the current disclosure, the ionization is likely to employ a carrier gas supply 58, assisting sample and dopant vapors delivery and adjusting pressure in the ionization region. Preferably, the source 53 is followed by an ion funnel interface 54, pumped to about 10 mBar gas pressure by a mechanical pump 55. In an embodiment, the IMS instrument further comprises two drift cells 56 and 57 operating on both sides of the ion gate, each drift cell has own collector 56C and 57C, preferably connected to a single acquisition system 58 (0.5-1 MHz ADC with at least 16 bit vertical resolution).

Since GC employ clean gases and delivers low volatile analyte, the mechanical design of the GC×GC-IMS several considerations are contemplated hereby. For example, in an implementation, the ion source and IMS components are preferably heated up to substantially at or between 250-300 C which facilitated an avoidance of an absorption of analyte molecules onto walls of the device. In addition, in an implementation, the IMS employs clean materials (e.g., non-porous metals, ceramics, and glass) to prevent fumes. For example, in some colder regions one may use Vespel and Kapton for insulation and graphite for seals. In an implementation, vacuum seals used therewith are metal-to-metal type (e.g., Conflat and Swagelock) which helps to avoid outgassing materials. In an implementation, drift cells may be a ceramic tube coated inside with a high impedance material, like tin oxide. Alternatively, a set of metal plate (e.g. ring) electrodes may be separated by ceramic balls and clamped by metal rods. Preferably, the electrode window should exceed the size of gate opening by at least one thickness of the plate. In one numerical example, the gate opening has 25 mm diameter, 4 drift electrodes are rings with 75 mm window and the drift region is 100 mm long. Preferably, a chain of resistors is located outside of the vacuum region. Preferably, the ion source region is at near ground potential, while the back of the drift tube is floated, and collector signal comes via a capacitor. Preferably, the drift cell is surrounded by a shroud (a) for helping to prevent gas steering by the gas flow in the ion source region and (b) to provide a slow (1 m/s) laminar flow within the drift cell in order to prevent source fumes into the drift region. To avoid piezo-effects on collector, in an embodiment, the mechanical pump is vibration-decoupled (e.g. by a bellow) and is substantially isolated therefrom by an oil filter to avoid oil fumes. For economy reasons, a small size mechanical pump may be used to allow bench-top packaging of the IMS detector for GC×GC.

Multi-Mode Source for GC×GC-IMS

Referring again to FIG. 5, the ion source 53 may be one of the group consisting of: (i) a photo-ionization (PI) source; (ii) a photo-chemical (PCI) ionization source 53PI with dopant vapors; (iii) a chemical ionization (CI) source with proton transfer reactions; (iv) a negative chemical ionization (NCI) source with electron attachment ionization; and (v) a glow discharge (GD) source 53GD with analyte ionization by conditioned products of glow discharge. In an implementation, chemical ionization (CI) is provided by inducing a corona or few uA (limited by resistor) glow discharge. Dopants like ammonia, acetone, or amino-benzene would generate quasi-molecular MH+ ions, ionizing analyte molecules by proton transfer reactions. In NCI source, M-H– or M– ions can be formed at negative corona bias. In an implementation, photochemical ionization (PI) 53PI is arranged by primary ionization of benzene or $CH_nCl_{4-n}$ with xenon or argon UV lamp. Analyte vapors are then ionized in charge transfer (electron tunneling) reactions, primarily forming molecular M+ ions. As described in PCT/US2011/048387, incorporated herein by reference, in a glow discharge (GD) source 53GD the glow discharge products are conditioned to let electrons and most of the ions drift to walls of the delivering tube, while longliving meta-stable Helium atoms with about 20 eV excitation ionize analyte vapors in a separate 'reactor' volume, thus forming molecular M+ ions with moderate amount of fragments. The composition of those fragment ions is similar to those formed by electron impact (i.e. could be used for NIST confirmation) though GD ionization is softer. Ion sources like CI may be switched in ionization polarity by reverting potential on ionizing corona discharge. Ion sources like PCI and GD are capable of simultaneous generation of both polarities ions and may be combined within one source via a common reactor chamber 53R. Ionization mode may be switched by regulating gas flows (shown by white arrows), or switching glow discharge or turning UV lamp on and off. Based on the described properties of CI, NCI, PI and GD sources, GC×GC-IMS 51 with rapidly switching multiple ionization modes is expected to provide several important analytically properties, such as: (i) characterization of analyte mass which is roughly correlate with ion mobility; (ii) an additional selectivity of ionization which carry such information as ionization potential, proton or electron affinity and presence of polar groups; and (iii) ability of ionizing wide range of analyte classes. Such ability may be considered as an additional analytical dimension.

The GC×GC-IMS instrument is provided to characterize complex mixtures and for detecting ultra-traces. The GC×GC is known to separate compounds by classes. In some samples, like diesel or crude oil, multiple isomers form characteristic patterns in two-dimensional (2D) space of retention times RT1 and RT2. Often, target compounds, like halogenated toxic compounds, are separated in 2D space from the majority of matrix compounds. It is expected that instant IMS spectra would be much less complicated compared to conventional direct IMS analysis. Then the information on the mobility of molecular ions may be obtained. Ion mobility is expected to become a third analytical dimension of the 3D GC×GC-IMS analysis.

Fast IMS with Fast MRTOF

In an embodiment, an accelerated IMS is coupled to a high resolution time-of-flight instrument which operates at frequent and coded pulsed injection, this way supporting high speed of the IMS separation.

Figure 6:
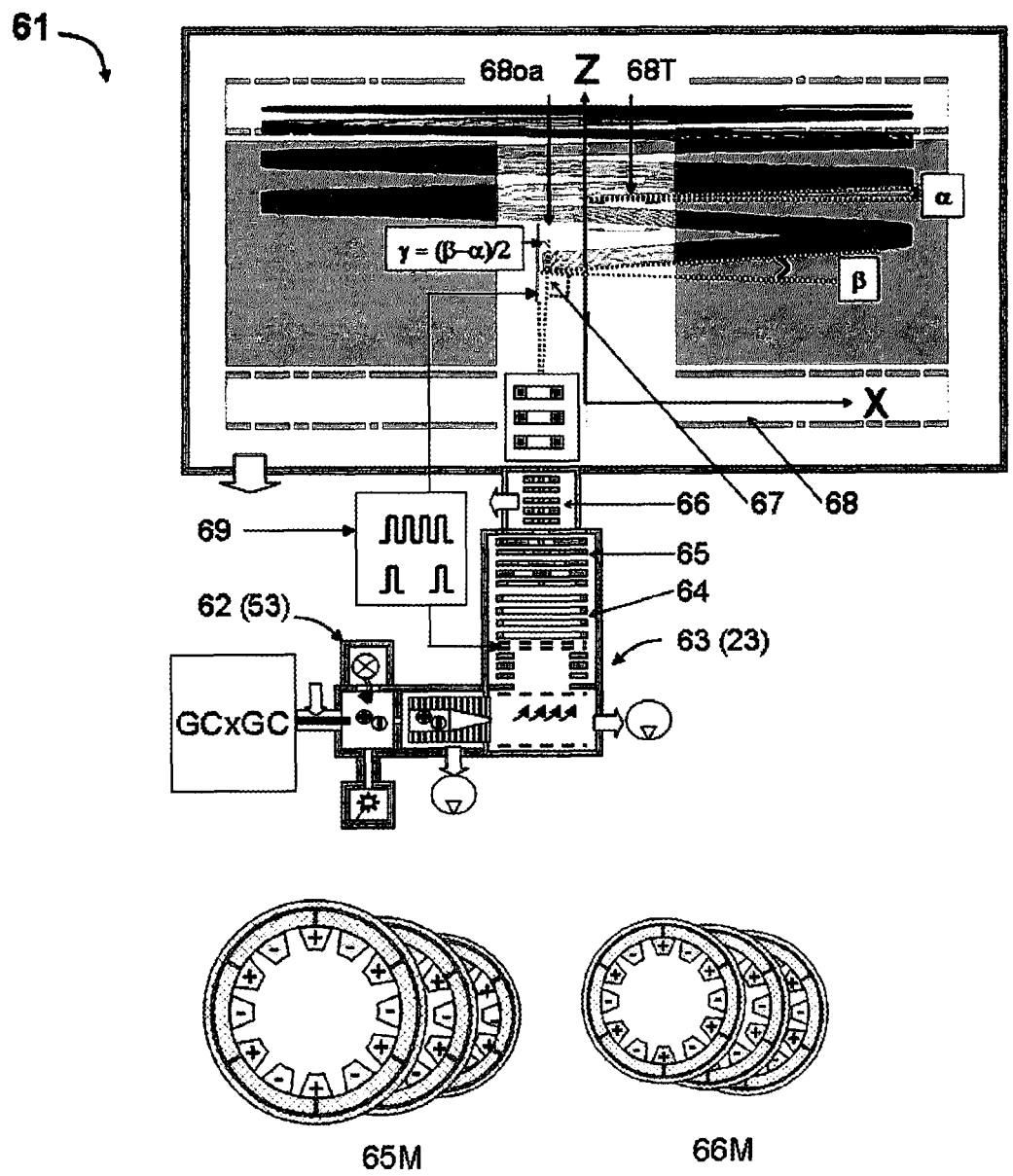
FIG. 6 depicts an embodiment of GC×GC-IMS-MRTOF with the fast pulse coded orthogonal accelerator.

Referring to FIG. 6, the IMS-TOF 61 comprises the following sequentially combined components: an above described multi-mode ion source 62 (53), an above described ion gate 63 (23), an ion drift tube 64 filled with gas at pressure from 1 to 100 mBar, a tapered IMS section 65 for converging an ion flow, a differentially pumped ion guide 66, an orthogonal accelerator 67 with fast coded pulsing at mean frequency exceeding 100 kHz; a multi-reflecting time-of-flight mass analyzer 68; and a data system 69 providing coded start signals with the string duration comparable to IMS separation time and also providing IMS-MS spectral decoding with the account of the coded pulse intervals. For the sake of rapid ion transition, said tapered IMS section 65 may comprise an ion funnel with a central expanding and contracting section 65T or a multipole set 65M with an axial DC gradient formed of multipole sections with a DC offset linearly changing along the multipole set, preferably made of PCB stack. Preferably, the ion guide 66 is made as multipole with an axial DC gradient, made of PCB stack 66M. Preferably, IMS-TOF 61 is preceded by a GC or GC×GC 70. The MR-TOF is preferably a cylindrical analyzer.

In an embodiment, GC×GC 70 separates analyte molecules and elutes them sequentially, wherein GC2 peak duration is about 30-50 ms. The ions source 62 (e.g., CI, PI, or soft GD) ionizes molecules and forms primarily M+ or MH+ ions. In an implementation, ion source 62 operates at gas pressures substantially at or between 100 and 1000 mBar and IMS substantially at or between 10 and 100 mBar. In an implementation, differential pumping is provided by mechanical pumps that may be equipped with fume filters which thereby forms gas flow between stages. Preferably, a gas jet is oriented parallel and with an offset from the gate to avoid gas steering. In an arrangement, a DC bias of the cap 23 drives ions towards mesh 24 and an RF signal between meshes 24 and 25, retards ions in the close vicinity of the meshes. As such, ions get stored within local traps in front of mesh 24. Periodically, a DC pulse is applied either to the cap 23 or to the back mesh 25 to extract short (about 10 us) ion packets. Ion packets are separated by mobility in the drift region 64, become converged in the tapered section 65, rapidly pass through the ion guide 66 (being driven by axial field), transfer into the pulsed extraction region 67, and geet pulsed accelerated into the cylindrical multi-reflecting TOF 68 for mass separation. The analyzer is expected to improve the duty cycle substantially at or between 2-3% and the operation speed substantially at 2 kHz compared to planar MR-TOF.

Because of employing MR-TOF with high resolution and low to sub-ppm mass accuracy while saving duty cycle by coded fast pulsing, the analytical method of FIG. 6 provides additional analytical dimensions without generally introducing any additional ion losses or losses in analysis speed. Sub-ppm mass accuracy allows determining accurate mass defect (dM) relative to integer mass, which in turn allows determining elemental composition for volatile and semi-volatile compounds with a limited mass (typically under 500) and limited choice of composing elements (such as C, O, H, N, S and halogens). One can also modify the method by introducing rapidly switching ionization modes as described in FIG. 5, or employ a rapidly switching in-source fragmentation, thus toggling between soft ionization and fragmentation modes.

Timing of IMS-TOF instrument 61 is a consideration as GC×GC operates with substantially rapid separation thereby forming generally wide peaks (e.g., 30-50 ms). The data system 69 periodically drives the IMS gate 63 and orthogonal extraction region 67 with an encoded pulse string, wherein the average period between TOF pulses is generally at or between 5 and 10 us, pulse string duration is generally at or between 1 and 2 ms, and spectra are averaged for about 10 ms. In an implementation, decoded spectra are expected to recover GC profiles and IMS separation in-spite of fairly long (e.g., at or between 1-2 ms) IMS separation and in-spite of long (e.g., ~0.5 ms) flight time in TOF.

Figure 7:
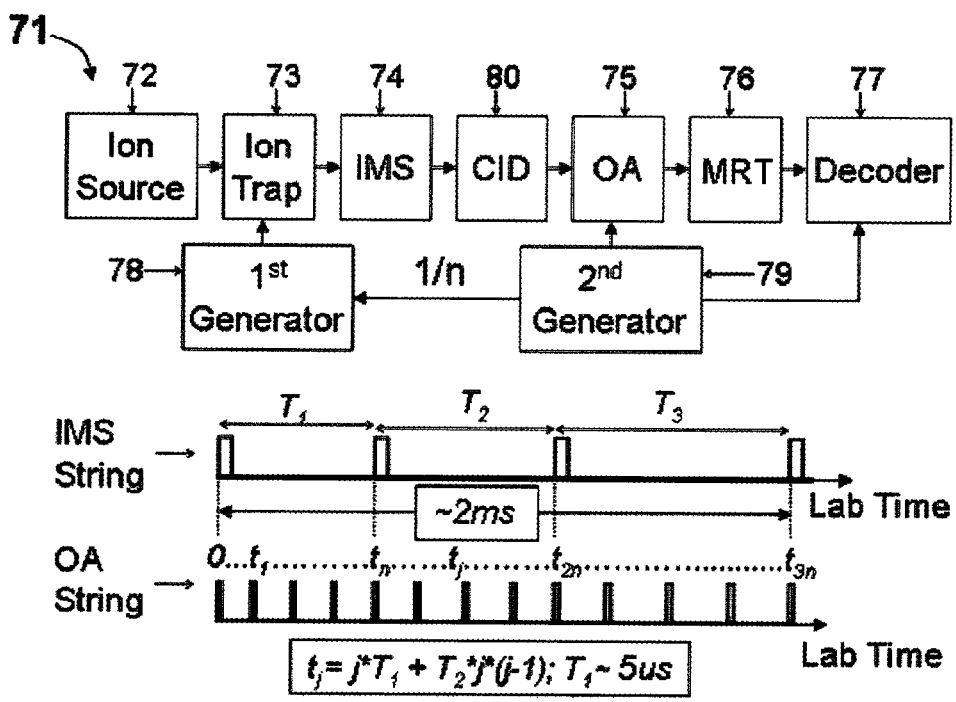
FIG. 7 depicts a block scheme and time diagram for apparatus of FIG. 6.

Referring now to FIG. 7, the tandem mass spectrometer 71 comprises: an ion source 72; an ion trap 73 (here dual RF mesh) being triggered by a first encoding pulse generator 78 which forms an IMS pulse string; an ion mobility spectrometer drift tube (IMS) 74 followed by a tapered section and by an ion guide with axial gradient (not shown); an orthogonal accelerator (OA) 75 being triggered by a second encoded pulse generator 79 which forms OA pulse string, an MR-TOF analyzer 76, and a data system with spectral decoder 77.

In an implementation, both pulse string generators 78 and 79 are substantially synchronized, e.g. first generator 78 may be triggered at every $n^{th}$ start of the second generator 79, having OA time string like $T_j = j*T_1 + T_2*j*(j-1)$ with uneven time intervals and $T_1 \sim 5\text{-}10$ us. The IMS string from generator 78 triggers ion injection from ion trap 73 into IMS drift region 74. The OA string triggers frequent OA firing such that to catch short packets (10-20 us) past IMS. In an implementation, the IMS string has one pulse only and the duration of the OA string matches the separation time within the IMS. The signal at the MR-TOF detector is summed for multiple IMS cycles for approximately 10 ms, such that to follow 30-50 ms peaks past GC×GC. In an implementation, every mass component is generally expected to form a series of at least several MR-TOF peaks corresponding to sequential OA firings. Then, because of unique intervals in the OA string, time intervals between peaks would allow deciphering both—actual OA firing time and flight time in MR-TOF. The overall spectrum is decoded for recovering multiple series and their overlaps. In the simplest decoding algorithm the overlaps are discarded. It is expected that for summed spectrum the spectral decoding would recover both—mobility time (and thus mobility), and the flight time in MR-TOF (and thus m/z). The speed of processing is preferably enhanced by multi-core PC boards or multi-core imbedded processors.

In another implementation, a more frequent IMS triggering is employed to enhance space charge limit of IMS and dynamic range of the TOF detector. In an embodiment, each IMS start corresponds to n OA starts. At spectra decoding, the confusion between multiple IMS shots is likely to be avoided due to significant correlation between mobility, charge and mass. Since ionic m/z is expected to be recovered from TOF spectra, and m/z spacing between isotopes would allow extracting charge state, then the ion mobility may be predicted with about 10-20% accuracy. This means that IMS may be fired five-ten times more frequently. Besides, the same TOF peak series are expected to repeat with the period of IMS firing and would be accounted at the stage of spectra decoding. The duration of the IMS string may be about 1-2 ms to match IMS separation time, and intervals between IMS pulses may be about 0.2-0.5 ms.

With continued reference to FIG. 7, tandem mass spectrometer 71 may further comprise a fragmentation cell 80 between IMS 74 and OA 75. The fragmentation may employ fragmentation methods including collision induced dissociation (CID), surface induced dissociation (SID), photo induced dissociation (PID), electron transfer dissociation (ETD), electron capture dissociation (ECD), and fragmentation by excited Rydberg atoms or ozone. In an implementation, the time diagram remains the same and the OA is operated with coded frequent pulsing (about 200 kHz) in order to track rapid changes of the ion flow after cell 80. Accordingly, the tandem mass spectrometer 71 can provide all-mass pseudo MS-MS. In such combination the IMS is used for crude (resolution substantially at or between 50-100) but rapid separation of parent ions and the MR-TOF is employed for even faster acquisition of fragment spectra. Optionally, in case of moderate ion flows, the encoding of the first generator may be switched off. Preferably, the fragmentation cell (usually RF device) is equipped with means for ion accumulation and pulsed extraction and the OA pulse string is synchronized for the duration of the extracted ion bunch. Algorithms for decoding the spectra may then be employed. For example, an algorithm is employed to search for MR-TOF peak series which are spaced according to encoded time intervals, then the system allocates overlaps between series and may either discard or account for such overlaps. Thereafter, each peak series allows allocating the corresponding OA start time and m/z of the component. The summed spectra are recorded with 100 Hz rate which allows recovering 30-50 ms profiles of GC×GC separation. Overall, the encoding allows compressing the time scale and obtaining 10 ms time resolution of GC×GC analysis and 10 us resolution of IMS analysis in-spite of nested analysis in fairly slow IMS and MR-TOF devices with 0.5-2 ms flight times.

Figure 8:
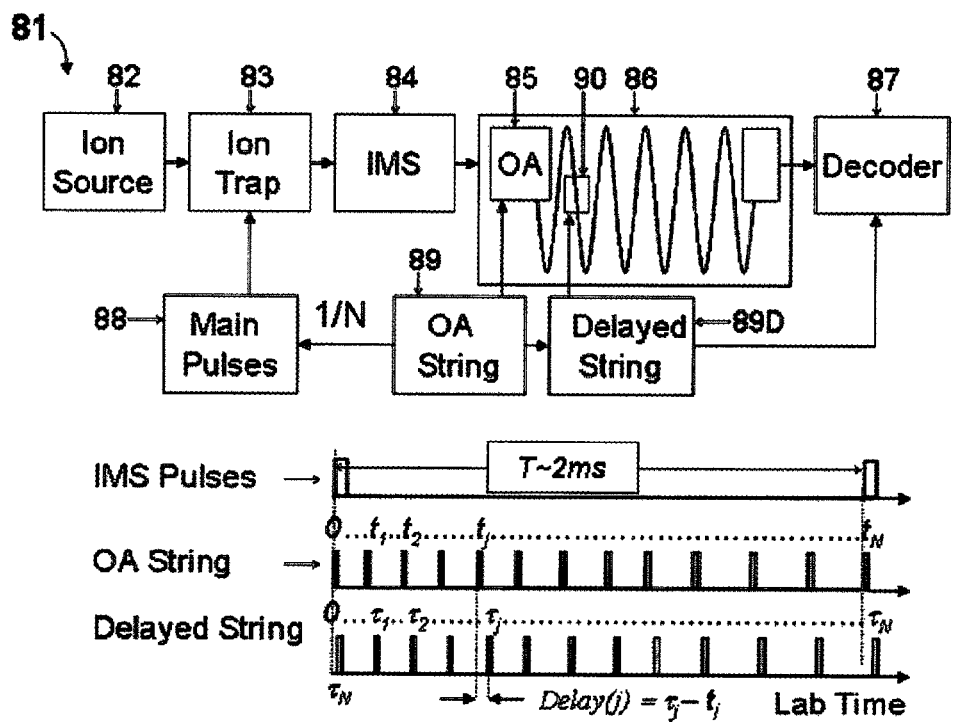
FIG. 8 depicts a block scheme and time diagram for IMS-MRTOF apparatus with timed selection in the MRTOF for the correlated mobility and m/z ion selection.

Referring to FIG. 8, another implementation 81 of tandem mass spectrometer comprises an ion source 82, an ion trap 83 triggered by main pulse generator 88, an IMS 84, an OA 85 being triggered by a second encoded string generator 89, an M-TOF analyzer 86, a spectral decoder 87, and a time gate mass selector 90 in the M-TOF analyzer 86, said time gate selector is triggered by a delayed string 89D. In an implementation, the main pulse generator 88 has period T~2 ms matching IMS separation time. The OA string generator 89 forms a string of N pulses with uneven intervals and with the total duration of the main generator $T=t_N$. The delayed string 89D is synchronized with the OA string generator 88, but has a variable delay of number j pulse $D_j$-$t_j$ which is proportional to the time $t_j$. The time selection gate 90 (e.g. a pulsed set of bipolar wires) is located after one ion cycle in the M-TOF 86 and is capable of passing through ions in the particular range of flight times, proportional to ions $(m/z)^{1/2}$. As a result, the selected ion m/z range becomes correlated with the IMS separation time $t_j$ to separate a particular class of compounds, or a particular charge state this way reducing chemical noise.

Referring back to FIG. 4-B, the dual RF mesh gate provides inverting time profiles by slow ramping of a DC field pushing ions through the gate. Since the effective potential of the RF barrier is mass dependent, the small m/z ions would pass first, which generates a mass inversion. With a proper match between the DC ramping speed and the IMS separation time one may align ions with a particular ratio between ions m/z and mobility at the entrance of the MR-TOF. Preferably, OA accepts only ions with a desirable ratio, such that to analyze only ions of the particular chemical class (for example aromatic compounds, while excluding linear molecules).

Multi-Dimensional Separations

The methods and systems described herein present examples of comprehensive analysis within multiple orthogonal analytical dimensions. 'Comprehensive' means that the analysis occurs in nested time scales (i.e. one separation does not affect timing and resolution of another separation). 'Orthogonal' means that separations do not correlate fully and provide mutually complimentary information. Multi-dimensional separation is expected to reduce interference between analyte species (initially injected as complex mixtures), to push for smaller detection limits, and to improve specificity and reliability of the identification.

In an implementation and as depicted in FIG. 5, the comprehensive analysis in the following four orthogonal analytical dimensions is provided: (i) GC1; (ii) GC2; (iii) ion mobility; and (iv) specificity of ionization by various ionization methods at switching polarity.

In an implementation and as depicted in FIG. 5, the comprehensive analysis in the following five orthogonal analytical dimensions is provided: (i) GC1; (ii) GC2; (iii) IMS; (iv) M/z; and (v) dM (see description of FIG. 6). The number of dimensions may be further increased by using multiple and rapidly switching ionization modes (vi-th dimension) and in-source fragmentation (vii-th dimension).

In an implementation and as depicted in FIG. 7, the comprehensive analysis in the following six orthogonal analytical dimensions is provided: (i) GC1; (ii) GC2; (iii) IMS of parent ions; (v) M/z of fragments; and (vi) dM of fragment ions. As illustrated, the number of dimensions can be increased by using multi-mode ionization.

In an embodiment, even if not using IMS separation, the comprehensive analysis still comprises the following five orthogonal analytical dimensions: (i) GC1; (ii) GC2; (iii) M/z; and (iv) dM. The fifth analytical dimension is a multi-mode ionization.

The described methods of comprehensive analysis within multiple analytical dimensions comprise at least four dimensions of the group: (i) gas chromatography—GC1; (ii) second and nested in time gas chromatography—GC2; (iii) multi-mode or switching polarity soft ionization like PI, CI or GD; (iv) fast switching in-source fragmentation is—CID; (v) ion mobility separation—IMS; (vi) ion fragmentation past IMS; (vii) mass spectroscopic measurements of integer mass—m/z; and (viii) accurate mass measurements with extraction of mass defect and of elemental composition—dM.

Although the present invention has been describing with reference to preferred embodiments, it will be apparent to those skilled in the art that various modifications in form and detail may be made without departing from the scope of the present invention as set forth in the accompanying claims.

What I claim is:

1. A ion mobility spectrometer comprising:
   an ion source;
   an ion gate having a front mesh and a back mesh;
   a radiofrequency (RF) generator connected to said front mesh;
   a switching DC signal connected to said back mesh; and
   an ion detector.

2. An apparatus as set forth in claim 1, wherein said ion source is adjacent to and substantially parallel to said front mesh and said back mesh.

3. An apparatus as set forth in claim 1, further comprising at least one RF ion guide arranged between said ion source and said ion gate, and wherein said RF ion guide is selected from the group consisting of: (i) an ion funnel; and (ii) a multipole ion guide with axial field.

4. An apparatus as set forth in claim 1, wherein said front mesh and said back mesh are arranged in parallel with one another.

5. An apparatus as set forth in claim 1, further comprising an upfront gas chromatograph and an ion drift space, wherein the region of said ion gate and of said drift space is pumped by a mechanical pump.

6. An apparatus as set forth in claim 1, wherein said ion source is selected from the group consisting of: (i) a photo-ionization source; (ii) a photo-chemical ionization source with a dopant; (iii) a chemical ionization source with proton transfer reactions; (iv) a chemical ionization source with electron attachment ionization; and (v) a glow discharge source with analyte ionization by conditioned products of glow discharge.

7. An apparatus as set forth in claim 1, wherein said ion source has means for switching between ionization modes or for switching between ion polarities.

8. An apparatus as set forth in claim 1, wherein said ion source has fragmentation means and means for switching said fragmentation at time scale of chromatographic separation.

9. An apparatus as set forth in claim 1, further comprising:
   a tapered IMS section for converging an ion flow;
   an orthogonal accelerator with fast coded pulsing at mean frequency exceeding 100 kHz;
   a multi-reflecting time-of-flight mass spectrometer; and
   a data system providing coded start signals with the string duration comparable to IMS separation time and also providing IMS-MS spectral decoding with the account of the coded pulse intervals.

10. An apparatus as set forth in claim 1, wherein said tapered IMS section comprises either an ion funnel with a central expanding and contracting section, or a PCB made multipole set with an axial DC gradient formed of multipole sections with a DC offset linearly changing along the multipole set.

11. A method of ion mobility spectrometric analysis comprising:
    generating ions within an ion source operating at a pre-defined gas pressure;
    forming a local RF field between first and second meshes while attracting ions toward the RF field region by a DC field, said first and second meshes being spaced apart by a pre-defined distance, wherein the DC field substantially prevents ion penetration through the barrier of said RF field thereby yielding ion localization in local RF traps around mesh cells;
    propelling ions through said RF field by a pulsed switch of a DC field in the region of said RF field thereby forming short ion packets;
    separating ions by their mobility within an electrostatic field; and
    detecting a time dependent signal on a detector.

12. A method as set forth in claim 11, wherein ions are introduced into the RF field region that is adjacent to and substantially parallel to said first and second meshes.

13. A method as set forth in claim 11, further comprising:
    undertaking an ion transfer between said ionization and said gating steps, wherein said ion transfer include a radiofrequency confinement of ions to thereby yield a difference between gas pressures and to avoid significant gas motion within the mobility separation stage.

14. A method as set forth in claim 11, further comprising:
    performing analyte separation using gas chromatographic separation.

15. A method as set forth in claim 11, further comprising:
    performing analyte separation using dual stage gas chromatographic separation.

16. A method as set forth in claim 11, wherein said step of ionization includes a step selected from the group consisting of: (i) photoionization; (ii) photo-chemical ionization with a dopant; (iii) chemical ionization with proton transfer reactions; (iv) chemical ionization with electron attachment ionization; and (v) analyte ionization by conditioned products of a glow discharge.

17. A method as set forth in claim 11, further comprising:
    switching between ionization methods or for switching between ion polarities.

18. A method as set forth in claim 11, further comprising:
    performing ion fragmentation switched on and off at a time scale of said chromatographic separation.

19. A method as set forth in claim 11, further comprising:
    spatial focusing of ion flow past said step of ion mobility separation;
    performing an orthogonal ion acceleration with repeatable strings of fast coded pulses at mean frequency exceeding 100 kHz;
    undertaking a time-of-flight analysis of ion m/z within a multi-reflecting electrostatic fields; and
    decoding information on ion mobility time, ion mass and ion intensity based with the account of the coded pulse intervals.

20. A method as set forth in claim 19, further comprising:
    performing ion fragmentation between steps of ion mobility separation and time-of-flight analysis.

21. A method as set forth in claim 19, further comprising:
    performing ion sequence inversion at slow ramping of DC field propelling ions through said RF barrier at said gating step.

* * * * *